United States Patent [19]
Esposito

[11] Patent Number: 5,997,811
[45] Date of Patent: Dec. 7, 1999

[54] METHOD FOR STERILE SYRINGE PACKAGING AND HANDLING

[75] Inventor: Dominick G. Esposito, Los Gatos, Calif.

[73] Assignee: Cohesion Technologies, Inc., Palo Alto, Calif.

[21] Appl. No.: 08/886,957

[22] Filed: Jul. 2, 1997

[51] Int. Cl.$^6$ .................................. A61L 2/00; A61L 2/08
[52] U.S. Cl. .................................. 422/1; 422/21; 422/22; 422/40; 53/425
[58] Field of Search .................................. 422/22, 24, 28, 422/21, 40, 294, 26, 1; 53/425, 426

[56] References Cited

U.S. PATENT DOCUMENTS

| | | | |
|---|---|---|---|
| Re. 25,113 | 1/1962 | Wilburn | 604/190 |
| 2,915,063 | 12/1959 | Cutter | 604/163 |
| 3,112,747 | 12/1963 | Cowley | 604/197 |
| 3,215,141 | 11/1965 | Podhora | 604/163 |
| 3,314,427 | 4/1967 | Stafford | 604/163 |
| 3,406,686 | 10/1968 | Keller | 604/197 |
| 3,435,944 | 4/1969 | Ishii | 206/365 |
| 3,473,646 | 10/1969 | Burke | 206/229 |
| 3,586,064 | 6/1971 | Brown | 141/1 |
| 3,625,353 | 12/1971 | Ishii | 206/365 |
| 3,654,925 | 4/1972 | Holderith | 604/413 |
| 3,685,248 | 8/1972 | Godelaine | 53/425 |
| 3,780,935 | 12/1973 | Lukacs et al. | 494/37 |
| 3,800,947 | 4/1974 | Smith | 210/117 |
| 3,937,219 | 2/1976 | Karakashian | 604/26 |
| 4,021,352 | 5/1977 | Sarstedt | 210/359 |
| 4,057,499 | 11/1977 | Buono | 210/136 |
| 4,142,668 | 3/1979 | Lee | 494/36 |
| 4,184,593 | 1/1980 | Dorr | 206/365 |
| 4,628,969 | 12/1986 | Jurgens, Jr. et al. | 422/25 |
| 4,818,386 | 4/1989 | Burns | 210/97 |
| 4,822,340 | 4/1989 | Kamstra | 604/135 |
| 4,828,716 | 5/1989 | McEwen et al. | 210/740 |
| 4,877,520 | 10/1989 | Burns | 210/94 |
| 4,878,903 | 11/1989 | Mueller | 604/199 |
| 5,286,257 | 2/1994 | Fischer | 604/82 |
| 5,308,506 | 5/1994 | McEwen et al. | 210/745 |
| 5,332,092 | 7/1994 | Fischer | 206/365 |
| 5,393,674 | 2/1995 | Levine et al. | 436/177 |
| 5,519,931 | 5/1996 | Reich | 29/426.3 |
| 5,597,530 | 1/1997 | Smith et al. | 422/28 |
| 5,638,661 | 6/1997 | Banks | 53/425 |

FOREIGN PATENT DOCUMENTS

WO 94/19038  9/1994  WIPO .

Primary Examiner—Elizabeth McKane
Assistant Examiner—Theresa T. Snider
Attorney, Agent, or Firm—Pennie & Edmonds LLP

[57] ABSTRACT

The present invention is directed to a method for the packaging and handling of sterile syringes. More specifically, a syringe and a syringe package are sterilized. The sterilized syringe is placed into the sterilized syringe package, which package is sealed to enclose the sterilized syringe. A fluid is introduced into the sterilized syringe. The sterilized syringe with fluid is then delivered into a sterile field by removing the syringe from the syringe package. The syringe package is preferably a peal-open sheath with a fitting member at one end. The fitting member extends partially into and partially out of the syringe package. It has a connector inside the syringe package for connecting to the sterile syringe, which connector is fluidly connected to an exterior connector. Thus, the fitting member provides a fluid connection from outside the syringe package to the enclosed sterile syringe.

7 Claims, 3 Drawing Sheets

METHOD FOR STERILE SYRINGE PACKAGING AND HANDLING

FIELD OF THE INVENTION

The present invention generally relates to a packaging for a sterile syringe which allows the sterile syringe to be handled while protecting the outer surface of the sterile syringe against contamination. More specifically, the present invention relates to a tear open and sterilizable packaging which can sealingly receive a sterile syringe and later be handled without concern for contaminating the sterility of the syringe or its contents. When the sterile syringe is needed, it can be directly released to a completely sterile environment. Therefore, the sterile syringe packaging of the present invention allows fluid processing to be conducted in a non-sterile environment and later delivers the sterile syringe in a sterile field with the least fluid transfer.

BACKGROUND OF THE INVENTION

A conventional process of obtaining a biological or other fluid samples such as a blood sample and transfer of such samples to a sterile field usually require multiple steps of fluid transfer with use of multiple devices. In particular, to preserve the sterility of the external surfaces of a syringe to be used in a sterile field, typically a sterile operator (e.g. operating room nurse) holds a sterile syringe while a non-sterile operator holds a non-sterile syringe, and the two must cooperate to dock the syringes and transfer the fluid into the sterile syringe.

In each fluid transfer, the syringe containing the fluid sample and other devices need to be sterilized or disinfected. Hence, such multiple steps and devices in preparation of the fluid sample can cause extra cost and time and overall inconvenience. In addition, risks of contamination of the sample and/or infection of the medical personnel can increase as the amount of handling and the number of devices increase.

Various U.S. patents disclose different syringe coverings for encasing syringes therein. However, these syringe coverings are usually designed to protect the encased syringes from contamination during transportation before such syringes are used for a fluid processing. None of these coverings allows the encased syringe to be used in various fluid processing, such as drawing a fluid, but still remain uncontaminated. Rather, these coverings only provide sterility during storage or during injection. Hence, fluid transfers will be necessary prior to delivering the encased syringe to a sterile environment.

In addition, U.S. Pat. No. 5,332,092 issued to Fischer discloses a syringe sheath for containing a syringe and preventing contamination of the syringe. The syringe in Fischer has an extruding portion which passes the sheath, via an aperture, to deliver a material. The extruding portion attached to the syringe can inevitably cause damages to the sheath during transportation of the syringe covering leaving the sterile syringe exposed to contamination. Further, when an aperture is provided on the sheath for passing through the extruding portion on the syringe, the same problem can occur as well.

SUMMARY OF THE INVENTION

In view of the above problems and disadvantages of the prior art, it is an object of the present invention to provide a device for use in fluid processing with the least number of fluid transfer steps in order to decrease handling by medical personnel, to reduce risks of contamination and to reduce the number of devices involved in the process to thereby minimize costs for obtaining such fluid sample.

It is a further object of the present invention to provide a device which provides a sterile syringe pre-filled with a fluid sample or which allows a sterile syringe for fluid processing in a non-sterile environment and the device can later deliver the sterile syringe containing the fluid sample to a sterile field with the least number of fluid transfer steps.

It is yet a further object of the present invention to provide a syringe packaging which protects a sterile syringe from contamination or infection in fluid transfer or processing.

The present invention relates to a sterile syringe package which comprises a sterile syringe having a syringe barrel and a luer or other suitable connector coupled to the syringe barrel. A sterile sheath is provided to sealingly enclose the sterile syringe and have an opening portion. The opening portion is defined by a surrounding edge portion of the sterile sheath. The sterile syringe package further comprises a fitting member removably connected to the luer connector of the sterile syringe. The fitting member is also sealingly fixed with the surrounding edge portion of the sheath to form an enclosed syringe chamber for housing the sterile syringe. Preferably, the sterile sheath of the sterile syringe package can be made of a radiation stable thermoplastic material or a breathable material sterilizable by gas or steam. The opening portion of the sterile sheath is adhered to the fitting member.

The fitting member of the sterile syringe package has a first and a second end and a body portion connected between the first and second ends. The first end of the fitting member is located in the syringe chamber for connecting to the luer of the syringe. The body portion of the fitting member is sealingly connected to the surrounding edge portion of the sheath.

According to the sterile syringe package of the present invention, a sterile envelope member can be further provided for sealingly enclosing the sheath and the fitting member to protect the same from contamination.

In a preferred embodiment, the sterile sheath of the sterile syringe package comprises a first and a second sheet. The two sheets are joined together along a sealing line, which is preferably an adhesive (or heat) sealing line. The sealing line discontinues to form the opening portion. The sterile sheath also has a tear off portion thereon. The tear off portion can overlap the sealing line.

In another preferred embodiment, the sterile sheath of the sterile syringe package is an elongate tube member with a first and a second end. The opening portion is located at the first end. The second end is adapted to seal the elongate tube member through a sealing line.

The present invention also relates to a sterile syringe packaging which comprises a sterile sheath for sealingly enclosing a sterile syringe having a luer or needle fitting. The sterile sheath has an opening portion defined by a surrounding edge portion of the sterile sheath. A fitting member is provided to be sealingly fixed to the surrounding edge portion of the sheath to thus form an enclosed syringe chamber for housing the sterile syringe. The fitting member is also adapted to be connected to the luer or needle fitting of the sterile syringe.

The fitting member of the sterile syringe packaging has a first and a second end and a body portion connected between the first and second ends. The first end of the fitting member is located in the enclosed syringe chamber for connecting to the luer or other suitable connector of the syringe. The body portion of the fitting member is sealingly connected to the surrounding edge portion of the sheath.

According to the sterile syringe packaging of the present invention, the sterile sheath has a tear off portion thereon. The sterile sheath comprises a first and a second sheet. The two sheets are joined together along a sealing line. The sealing line discontinues to form the opening portion.

The present invention relates to a sterile syringe package assembly which comprises a sterile syringe including a syringe barrel and a luer or needle fitting coupled to the syringe barrel. A sterile sheath sealingly encloses the syringe and has an opening portion defined by a surrounding edge portion of the inner sterile sheath. A fitting member is removably connected to the luer or needle fitting of the syringe and sealingly fixed to the surrounding edge portion of the sheath to form an enclosed sterile syringe package. The sterile syringe package assembly further comprises a sterile envelope member sealingly enclosing the sterile syringe package or a sterile barrier closure (e.g. a plug) can be fitted for the second end of the fitting member.

The present invention relates to a method for sterile handling of a syringe. The method comprises the steps of (a) sterilizing a syringe; (b) sterilizing a syringe package, which package is adapted to receive and encase the syringe in a sterile manner while permitting operation of the syringe; (c) enclosing the syringe in the syringe package within a first sterile environment; (d) removing the syringe package containing the syringe from the first sterile environment; (e) introducing a fluid into the syringe contained in the syringe package; and (f) delivering the syringe into a second sterile environment by removing the syringe from the syringe package. Alternatively, the syringe and package may be first assembled and then sterilized by irradiation or by gas or steam. The method of the present invention further comprises the step of processing the fluid within the syringe while the syringe is contained in the syringe package.

BRIEF DESCRIPTION OF THE DRAWINGS

These and other features, aspects, and advantages of the present invention will become much more apparent from the following description, appended claims, and accompanying drawing, in which:

DETAILED DESCRIPTION OF THE INVENTION

Figure 1:
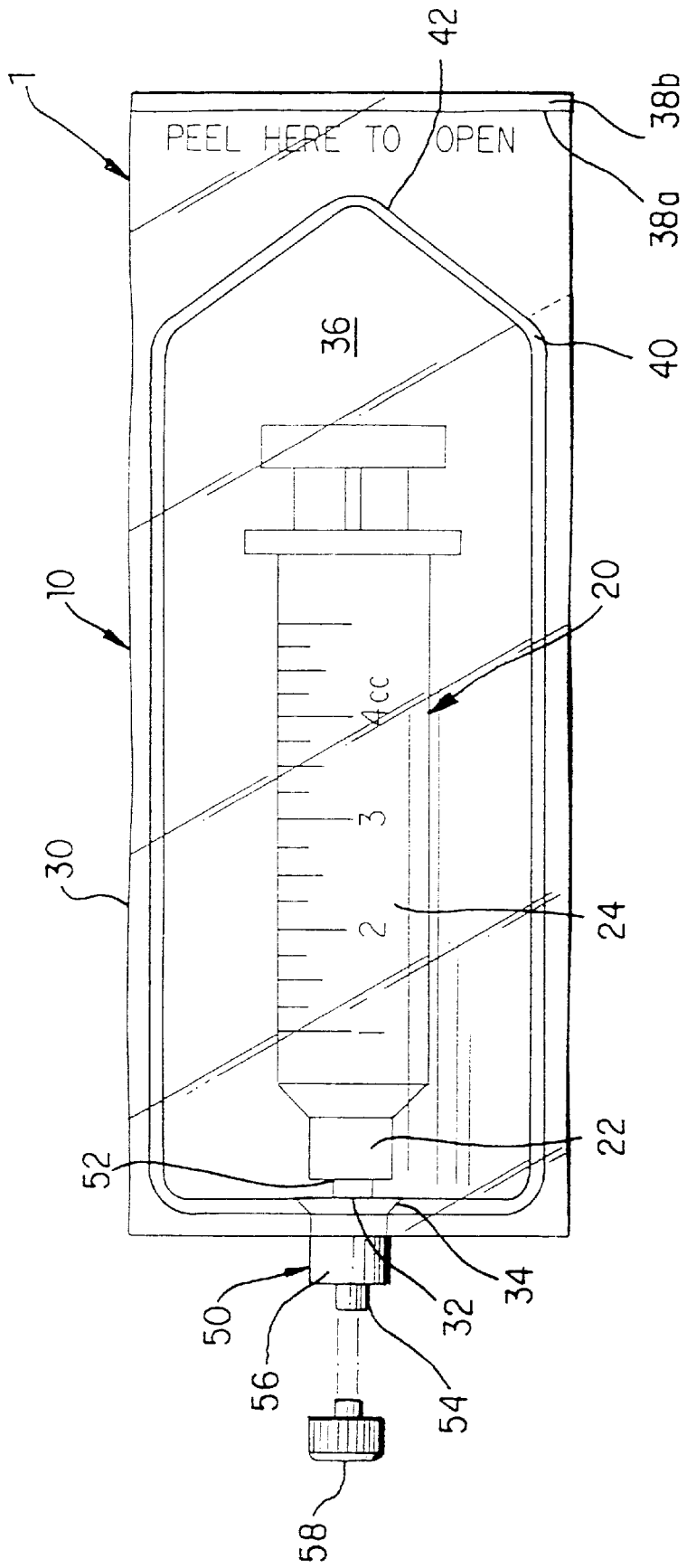
FIG. 1 is a plan view of a sterile syringe package of the present invention.
Figure 2:
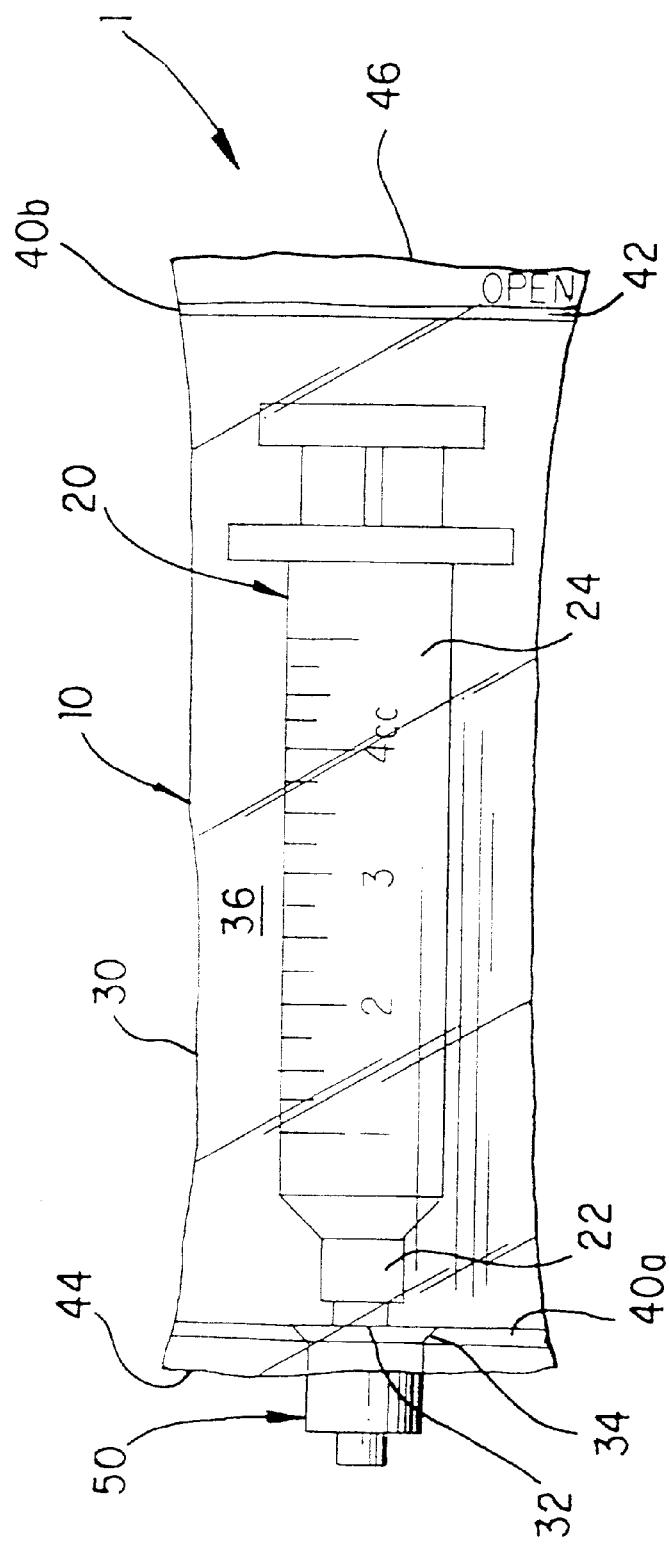
FIG. 2 is a plan view of an alternative preferred embodiment of the present invention.
Figure 3:
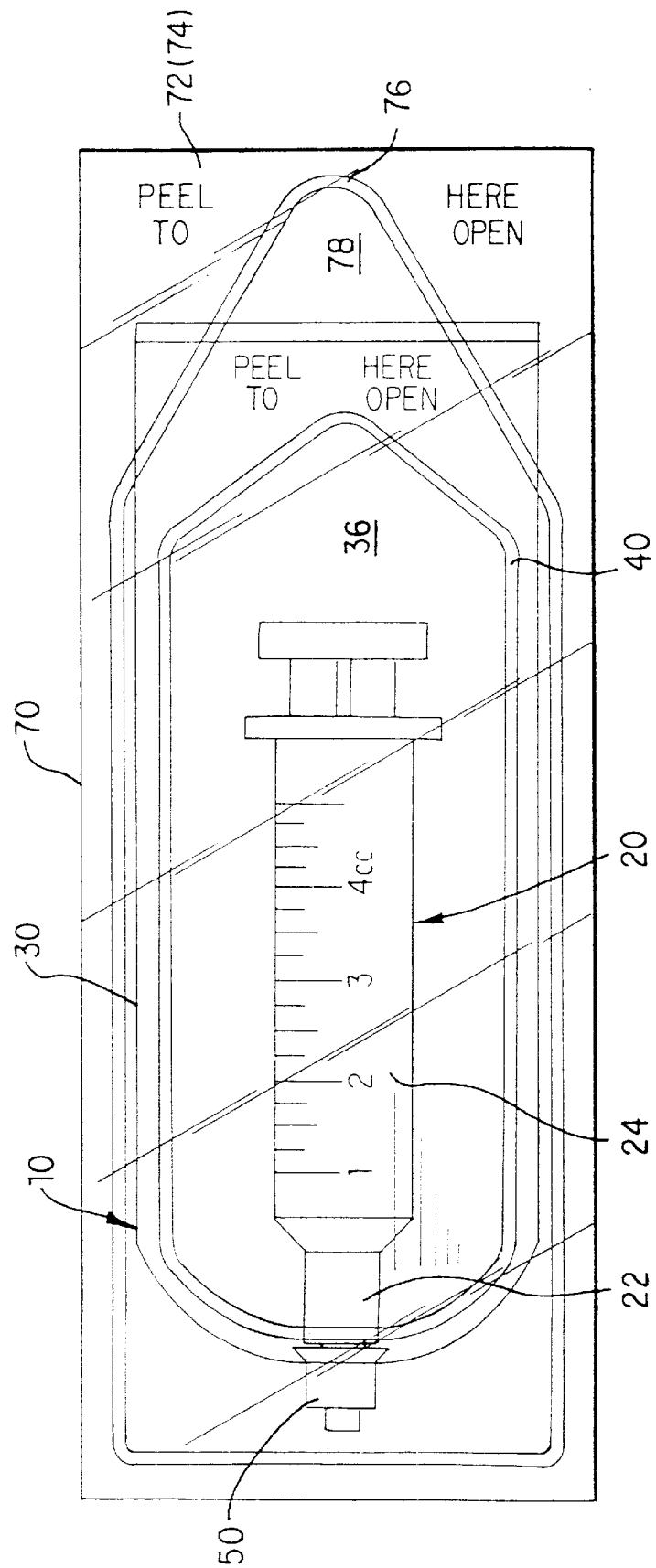
FIG. 3 is a plan view of a sterile syringe package assembly of the present invention.

Various sterile syringe packages and sterile syringe package assemblies embodying the principles of the present invention are illustrated in FIGS. 1–3. In each embodiment, the same elements are designated with the same reference numerals and repetitive descriptions are omitted.

Referring to FIGS. 1 and 2, a sterile syringe package of the present invention is generally designated by numeral reference 1. The sterile syringe package 1 has a sterile packaging 10 sealingly enclosing a sterile syringe 20 for protecting the sterile syringe 20 against contamination in fluid processing. Hence, the enclosed sterile syringe 20 can be handled without concern for contaminating the sterility of the syringe 20. When it is necessary to use the sterile syringe 20, the packaging 10 can be removed to deliver the sterile syringe 20 to a sterile field without fluid transfer.

The sterile syringe packaging 10 of the sterile syringe package 1 can be in the form of a pouch. It includes a sterile sheath 30 and a fitting member 50 which can sealingly enclose the sterile syringe 20. The sterile sheath 30 has an opening portion 32, which is defined by a surrounding edge portion 34 of the sterile sheath 30. The fitting member 50 is sealingly fixed with the surrounding edge portion 34 of the sheath 30 to form an enclosed syringe chamber 36 for housing the sterile syringe 20. The fitting member 50 is also adapted to be removably connected to a connector luer 22 coupled to a syringe barrel 24 of the sterile syringe 20.

The fitting member 50 can have a first and a second end 52, 54 and a body portion 56 connected between the first and second ends 52, 54. The body portion 56 of the fitting member 50 is adapted to be sealingly connected to the surrounding edge portion 34 of the sheath 30. Various conventional sealing methods, such as adhesives or thermal bonding, can be used for such connection. When the fitting member 50 is connected to the sheath 30, the first end 52 of the fitting member 50 is located in the syringe chamber 36 for connecting to the connector 22 of the syringe 20. The second end 54 of the fitting member 50 is adapted to receive an injection device, such as a second syringe, for introducing a fluid into the sterile syringe 20. Also, sterile barrier closure 58 may be fitted to the second end 54. Connector 22 and ends 52 and 54, may be provided as male or female luers or other suitable connectors in order to sealingly provide sterile fluid transfer connections as described herein.

In a first preferred embodiment as shown in FIG. 1, the sterile sheath 30 comprises a first and a second sheet 38a, 38b. The first and second sheets 38a, 38b are preferably about the same size and shape and therefore are overlapped with each other for the most part thereof. The two sheets 38a, 38b are adapted to be joined together along a sealing line 40 to form the enclosed syringe chamber 36. The sealing line 40 discontinues at the opening portion 32. It is understood that various conventional methods can be used to join the two sheets 38a, 38b. In particular, when the two sheets 38a, 38b are made of a thermoplastic material, methods such as heat or adhesive sealing may be used.

The sterile sheath 30 can have a tear off portion 42 thereon. Therefore, the sterile sheath 30 can simply be torn open or peeled open by the user to deliver the sterile syringe 20 to a sterile environment. In the preferred embodiment shown in FIG. 1, a peel-open type of sheath 30 is adopted. In such a case, the tear off portion 42 overlaps at least a portion of the sealing line 40. When being peeled open, the sealing line 40 breaks so that the first and second sheets 38a, 38b can depart from each other therealong.

There is provided an easy access in assisting the peeling action. In a preferred embodiment shown in FIG. 1, the first and second sheets 38a, 38b are purposely designed to be uneven at one end thereof. On the right side of the drawing, the second sheet 38b is slightly longer than the first sheet 38a. The staggered right ends of the two sheets 38a, 38b make it easier to separate the two sheets 38a, 38b when opening the sterile sheath 30. Other mechanisms facilitating in separating the two sheets 38a, 38b can also be used. Further, words and graphics can be used to identify the location of such easy access. Alternatively, an easy access mechanism can be used for a tear-open type sheath 30.

In another preferred embodiment as shown in FIG. 2, the sterile sheath 30 is an elongate tube member with a first and a second end 44, 46. The second end 46 is open until the sterile syringe 20 is inserted in the elongate tube member 30. The first and second ends 44, 46 each are sealed through a sealing line 40a, 40b to form an enclosed syringe chamber 36. The sealing line 40a at the first end 44 discontinues at the opening portion 32. Similar to the above description, the first and second ends 44, 46 can be sealed by various conventional methods. In particular, when the elongate tube member 30 is made of a thermoplastic material, methods such as heat or adhesive sealing may be used. One advantage of this preferred embodiment is that relatively short sealing lines 40a, 40b will be sufficient for sealing the sheath 30 to form an enclosed syringe chamber 36.

The second end 46 of the elongate tube member 30 has a tear off portion 42, which can overlap with the sealing line 40b at the second end 46. Various conventional tear off mechanisms can be applicable for the tear off portion 42. In an alternative embodiment, peel-open type portion similar to that in the first preferred embodiment can also be used at the second end 46 of the elongate tube member 30.

When using a syringe packaging 10 to protect a sterile syringe 20, the syringe packaging 10, at least the interior thereof, is to be sterilized. A syringe 20 is then placed in the syringe packaging 10 in a sterile environment. Syringe 20 may be sterilized before or after being placed in the syringe packaging 10. The sterile syringe 20 can generally have a syringe barrel 24 and a luer or needle fitting 22 coupled to the syringe barrel 24. It is to be noted that a needle may be left out from the syringe 20 in order to avoid any damage it can cause to the syringe packaging 10.

Before removing the syringe packaging 10 containing a sterile syringe 20 therein out of the same sterile environment, the syringe packaging 10 is properly sealed along the sealing line 40, or 40a, 40b to from a sterile syringe package 1. The syringe packaging 10 can protect the sterile syringe 20 from any contamination or disinfection. Therefore, the syringe package 1 can be handled in various fluid processing without any concern for contaminating the sterile syringe 20.

In a preferred embodiment of the present invention, a fluid can be introduced into the sterile syringe 20 encased in the syringe packaging 10. Since the encased syringe 20 does not have a needle thereon for the above reasons, another syringe or other fluid source (not shown) can be employed to inject the fluid into the encased syringe 20 through the fitting member 50 of the syringe packaging 10 and the luer or needle fitting 22 of the syringe 20. Then, the syringe package 1 may be subjected to subsequent processing including transportation.

After various fluid processing being conducted with the sterile syringe 20, it can be directly delivered to a sterile environment by removing the syringe packaging 10. In general, the packaging may be opened by the non-sterile operator to expose the sterile syringe while the non-sterile operator holds it through the packaging. The sterile operator may grasp the sterile syringe and remove it from fitting member 50 without compromising the sterility of the syringe. According to the first preferred embodiment, the first and second sheets 38a, 38b are peeled open to break the sealing line 40. The sterile syringe 20 is thus exposed and can be moved to a sterile environment. Alternatively, as shown in the second preferred embodiment, the tear off portion 42 is separated from the rest of the elongate tube member 30 to release the sterile syringe 20 into a sterile environment.

For further protection of the syringe package 1, an envelope member 70 is provided to encase the same. The envelope member 70 can be constructed similarly to the syringe sheath 30 as described hereinabove but have a larger size. According to a preferred embodiment as shown in FIG. 3, the envelope member 70 has two covering members 72, 74 made of the same size and shape. The two covering members 72, 74 are joined with each other along a continuous sealing line 76 forming an enclosed chamber 78. Such enclosed chamber 78 of the envelope member 70 is used to encase the syringe package 1, which is also sterilized before or after being placed therein.

In an alternative embodiment, the sterile syringe package 1 may also comprise a needle and a needle covering (not shown) removably attached to the fitting member 50. To protect the needle and needle covering from contamination, an outer pouch enclosing the sterile syringe package 1, including the needle 80 and the needle covering 82, may be provided. The outer pouch may be of similar construction as that for the encovlope member 70.

The foregoing description is only illustrative of the principle of the present invention. It is to be recognized and understood that the invention is not to be limited to the exact configuration as illustrated and described herein. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A method for sterile handling of a syringe comprising the steps of:

sterilizing a syringe;

sterilizing a syringe package, which package is adapted to receive and encase the syringe in a sterile manner while permitting operation of the syringe;

enclosing the syringe in the syringe package;

introducing a fluid into the syringe contained in the syringe package; and delivering the syringe into a sterile environment by removing the syringe from the syringe package.

2. The method of claim 1, wherein said syringe is first enclosed in said syringe package and said sterilizing steps are accomplished by sterilizing the syringe and the syringe package together.

3. The method of claim 2, wherein said sterilizing steps are accomplished by irradiating the syringe and the syringe package together.

4. The method of claim 1, wherein said delivering comprises:

a non-sterile operator holding the outside of the syringe package and opening said package to expose said syringe; and a sterile operator grasping said syringe to remove it and introduce it to the sterile environment.

5. The method according to claim 1, wherein said syringe package comprises a sheath with an opening portion; and a fitting member sealingly fixed within said opening portion, said fitting member for receiving the syringe and providing fluid communication to the syringe in said sheath.

6. A method for sterile handling of a syringe comprising the steps of:

sterilizing a syringe;

sterilizing a syringe package, which package is adapted to receive and encase the syringe in a sterile manner while permitting operation of the syringe;

enclosing the syringe in the syringe package; introducing a fluid into the syringe enclosed in the syringe package after said sterilizing steps and said enclosing step; introducing a fluid into the syringe enclosed in the syringe package said sterilzing steps and said enclosing step; and delivering the syringe containing said fluid to a site of interest.

7. The method according to claim 6, wherein said site of interest is a sterile environment and said delivery step comprises delivering the syringe into the sterile environment by removing the syringe from the syringe package.

* * * * *